United States Patent [19]
Kutney et al.

[11] Patent Number: 6,071,714
[45] Date of Patent: Jun. 6, 2000

[54] PROCESS FOR THE MICROBIAL CONVERSION OF PHYTOSTEROLS TO ANDROSTENEDIONE AND ANDROSTADIENEDIONE

[75] Inventors: James P. Kutney; Radka K. Milanova, both of Vancouver, Canada; Christo Dimitrov Vassilev, Razgrad, Bulgaria; Svetoslav Stefanov Stefanov, Razgrad, Bulgaria; Natalya Velikova Nedelcheva, Razgrad, Bulgaria

[73] Assignee: Forbes Medi-Tech, Inc., Vancouver, Canada

[21] Appl. No.: 09/048,432

[22] Filed: Mar. 26, 1998

[51] Int. Cl.[7] .............................. C12P 33/00; C12P 33/16
[52] U.S. Cl. ................ 435/52; 435/55; 435/822
[58] Field of Search ................ 435/52, 55, 822

[56] References Cited

U.S. PATENT DOCUMENTS

| | | |
|---|---|---|
| 3,684,657 | 8/1972 | Kraychy et al. . |
| 4,057,469 | 11/1977 | Nishikawa et al. .................. 435/55 |
| 4,124,607 | 11/1978 | Beaton ................................ 552/545 |
| 4,223,091 | 9/1980 | Imada et al. ........................ 435/55 |
| 4,546,078 | 10/1985 | Manecke et al. ................... 435/52 |
| 4,923,403 | 5/1990 | Ferreira ............................... 435/52 |

OTHER PUBLICATIONS

W.J. Marcheck, S. Krachy and R.D. Muir, Appl. Microbiol., 23, 72 (1972).

A.H. Conner, M. Nagaoka, J.W. Rowe and D. Perlman, Appl. and Environ. Microbiology., 32, 310 (1976).

K. Kieslich, J. Basic Microbiol., 25, 461 (1985).

*Primary Examiner*—Herbert J. Lilling
*Attorney, Agent, or Firm*—ipsolon llp

[57] ABSTRACT

A novel process for the fermentation of phytosterol compositions to androstenedione (androst-4-ene-3,17-dione, AD) and/or androstadienedione (androsta-1,4-diene-3,17-dione, ADD) is disclosed. The process utilizes the micro-organism Mycobacterium MB 3683, and selected suitable solubilizing agents such as polypropylene glycol or silicone for solubilizing the phytosterol compositions at high concentrations in the nutrient medium. The innoculum of Mycobacterium MB 3683 is grown in a nutrient medium comprising Refiners molasses and inorganic salts.

10 Claims, No Drawings

PROCESS FOR THE MICROBIAL CONVERSION OF PHYTOSTEROLS TO ANDROSTENEDIONE AND ANDROSTADIENEDIONE

FIELD OF THE INVENTION

This invention relates in general to fermentation processes, and in particular to the bio-conversion of phytosterol compositions to androstenedione and/or androstadienedione.

BACKGROUND OF THE INVENTION

The microbial conversion of phytosterols (most frequently derived from soy bean oil) by various strains of bacteria is a well known process that has been used for the commercial production of androstenedione (AD) and androstadienedione (ADD) since the mid 1970's. In general, the known fermentation process involves the propagation of a mutant of Mycobacterium in an appropriate nutrient medium, transfer of the culture to a bioreactor containing the phytosterols, and then allowing the biotranformation to AD and/or ADD over a period of approximately 120 hours. Harvesting of the fermentation broth, extraction of the latter with an organic solvent, and subsequent crystallization in an organic solvent, generally provides the products AD and/or ADD as white crystalline powders. Pertinent references that discuss the known process and summarize the earlier studies are as follows:

S. Kraychy, and R. D. Muir, U.S. Pat. No. 3,684,657 (1972). W. J. Marsheck, S. Kraychy and R. D. Muir, Appl. Microbiol., 23, 72 (1972).

A. H. Conner, M. Nagaoka, J. W. Rowe and D. Perlman, Appl. and Environ. Microbiol., 32, 310 (1976).

K. Kieslich, J. Basic Microbiol., 25, 461 (1985).

One of the problems associated with the known phytosterol bio-conversion process (which problem plagues the entire steroid industry) involves the poor solubility of the substrate, in this case a phytosterol composition, in the aqueous nutrient medium. Inadequate solubility dictates the presence of only relatively low concentrations of substrate in the nutrient medium, resulting in poor contact with the micro-organism and generally leading to low yields of end products. Long fermentation times are also typically needed to achieve any satisfactory degree of bio-conversion.

Another problem associated with the known phytosterol bio-conversion process is that the end-product of the bio-conversion from phytosterols (or compositions of phytosterols) typically contains significant amounts of both AD and ADD. Given the similar chemical structure of AD and ADD, it is difficult and expensive to subsequently separate these two steroid products from one another.

A further problem associated with the known phytosterol bio-conversion process is that the micro-organism used to effect the bio-conversion (typically a mutant of Mycobacterium) is grown and propagated in nutrient media that are typically expensive to manufacture.

SUMMARY OF THE INVENTION

A solution to the solubility problem involves the use of selected suitable solubilizing agents that allow the phytosterol composition to be dissolved to form a clear solution, thereby allowing excellent contact with the micro-organism utilized in the bio-conversion, Prior-known solubilizing agents such as sunflower oil have been found to be only marginally effective. One aspect of the present invention involves the development and use of highly effective solubilizing agents for the bio-conversion of a variety of phytosterol compositions to AD and/or ADD. The phytosterol compositions themselves may be obtained from a by-product of the wood pulping process (know as "Tall Oil soap"), from any of the common vegetable oils (including for example soy, rapeseed, corn, cottonseed, sunflower, olive, linseed, and rice bran), or from a mixture of the above sources.

These selected suitable solubilizing agents, which include members of the glycol family and members of the silicone family, allow high concentrations of phytosterols to be dissolved in the nutrient medium. This provides for excellent contact with the micro-organism, reduces fermentation times, and affords relatively high yields of end-products.

In accordance with another aspect of the invention, Mycobacterium MB 3683 is utilized to effect the bio-conversion of a phytosterol composition to AD and/or ADD. It has been found that bio-conversions utilizing Mycobacterium MB 3683 to ferment phytosterol compositions to AD yield an end product that is significantly free of ADD; conversely, bio-conversions utilizing Mycobacterium MB 3683 (ATCC number PTA-352, deposited at the ATCC, 10801 University Blvd., Manassas, Va., on Jul. 14, 1999) to ferment phytosterol compositions to ADD yield an end product that is significantly free of AD.

In accordance with a further aspect of the invention, the micro-organisms used to effect the bio-conversion are grown and propagated in a nutrient medium comprising Refiners molasses and inorganic salts.

DETAILED DESCRIPTION

According to one preferred process, the specific solubilizing agents are within the family of glycols. Solubilizing agents within the glycol family, such as polypropylene glycol (PPG), allow for the solubility of high concentrations of phytocterols and, in turn, their efficient bioconversions to AD and/or ADD. For example, as shown in Table 1, successful bioconversions of phytosterol compositions to AD under various conditions have been completed. In representative trials, the concentration of the phytosterol composition has varied from 5 to 3 grams per liter of nutrient medium. To improve the interaction between the phytosterol composition and the micro-organism, the phytosterol composition is dissolved in a selected quantity of PPG (for example, 100 grams or one kilogram per liter of PPG) and the conversion yields to AD determined as shown in Table 1.

Of particular significance in this process is the much higher concentration of phytosterol composition (30 grams or more per liter of nutrient medium) that can be converted to AD. The normal concentration employed in industrial fermentations in accordance with the known phytosterol bio-conversion process is 10 grams per liter of nutrient medium.

Examples 1 and 3 illustrate that when PPG is utilized as the solubilizing agent, the inventive process allows conversion of various compositions of phytosterols derived from different sources. Example 1 describes the successful conversion to AD utilizing a phytosterol composition obtained from the "Tall Oil soap" by-product of the pulp and paper industry, while Example 3 shows the conversion of a phytosterol composition obtained from rapeseed oil.

The above-noted Examples also reveal that the mutant of Mycobacterium designated as MB 3683 is capable of converting these different phytosterol compositions, which vary in the relative ratios of their main components (including for example beta-sitosterol, campesterol, stigmastanol, stigmasterol, brassicasterol) to AD. It is evident from these Examples that various phytosterol compositions derived from pulp and paper industry derived by-products and/or from any of the various common vegetable oils, all of which contain these common phytosterols in differing ratio, can be utilized for bio-conversion to AD.

In another preferred process, as exemplified in Example 2, the specific solubilizing agents are within the silicone family. As is the case with solubilizing agents within the glycol family, solubilizing agents within the silicone family allow for the solubility of high concentrations of phytosterols and, in turn, their efficient bioconversions to AD and/or ADD.

In all of the Examples cited, the innoculum of micro-organism is initially grown in a nutrient medium comprising Refiners molasses and inorganic salts prior to transfer to the bioreactor in which the bio-conversion is performed.

Successful bio-conversions are achieved when the phytosterol composition is heated in the presence of the selected suitable solubilizing agent to form a paste-like consistency, and the latter is then added to the bioreactor containing the micro-organism and an appropriate inorganic salt medium.

During the fermentation process, it is important to maintain a temperature in the range of about 30–35° C. Monitoring of the pH during the fermentation reveals that the pH can vary in the range of approximately 7.0 in the initial period to approximately 4.7 at harvest time.

As shown in Table 1, the fermentation period can vary from about 6–25 days, depending in part on the quantity of phytosterol composition (in grams per liter of medium in the bioreactor) to be bio-converted to the end products.

The yields of AD produced can vary depending on fermentation conditions, but yields of 80–90% can be readily achieved as shown in Table 1 (Experiment Nos. 7–10). Experiment No. 10 is particularly impressive, with a yield of 80% AD at a level of 30 grams of phytosterol composition per liter of medium. As noted above, the level of phytosterol composition generally employed in the known phytosterol bio-conversion process is 10 grams per liter of medium.

The use of a vegetable oil (for example sunflower oil) as solubilizing agent (Experiment Nos. 1, 2, 5), generally leads to a much lower yield of AD. It has been found that the use of vegetable oil as solubilizing agent is in fact detrimental to the yield of AD, even when it is mixed with PPG (Experiment No. 11) as the solubilizing agent.

Examples 1 to 5 below represent specifically successful laboratory trials. However, each can be extrapolated to industrial-scale application using known industrial techniques to implement the invention as described herein.

EXAMPLE 1

The innoculum of Mycobacterium MB 3683 is prepared in four 2-liter Erlenmeyer flasks, each containing 500 ml of the following medium (gm/liter): Refiners molasses (54 ml), $NaNO_3$ (5.4 gm), $NH_4H_2PO_4$ (0.6 gm), glucose (6.0 gm). The pH of the medium is 7.0. The mixture is allowed to grow for a period of 2–3 days.

The phytosterol composition obtained from "Tall Oil soap" (100 gm) in polypropylene glycol (0.8–1 liter) is heated to 100–130° C. until a creamy paste-like solution is obtained. This solution is added to a 50-liter bioreactor containing 15 liters of salt medium containing the following (gm/liter); $NH_4NO_3$ (2 gm), $KH_2PO_4$ (1 gm), $Na_2HPO_4$ (2 gm), KCl (0.2 gm), $MgSO_4$ (0.2 gm), $CaCl_2$ (0.3 gm), and the following microelements, added at the level of 1 mL/liter of salt medium, and withdrawn from the following typical stock solution (gm/liter): $ZnSO_4$ (11 gm), $MnSO_4$ (6 gm), $FeSO_4$ (1 gm), $CoCl_2$ (0.3 gm), $CuSO_4$ (0.04 gm), $H_3BO_3$ (0.03 gm), KI (0.001 gm).

The entire contents in the bioreactor are sterilized a 120° C. and cooled to room temperature. The above-noted innoculum is now added to this bioreactor and the fermentation allowed to proceed for 120–144 h at 35° C. During this period, the initial pH of 7.0 varies to 4.7–5.5 at harvest time. GLC (see, for example, Experiments 6 and 7, Table 1). Extraction of the fermentation mixture with chloroform affords an extract containing polypropylene glycol and a mixture of AD/ADD in a varying ratio of 9:1 to 7:3 respectively.

EXAMPLE 2

The innoculum is prepared as in Example 1, but with a shorter growth period (2 days), in a single 2-liter flask containing 500 ml of the above-noted medium. This innoculum is then transferred to a 10-liter bioreactor containing 5 liters of the following "seed" medium (gm/liter) molasses (54 gm), $KNO_3$ (5.4 gm), $NH_4H_2PO_4$ (0.6 gm), sunflower oil (20 ml). After allowing growth in the bioreactor for a period of 12–16 h, a portion (1.5 liters) of this innoculum is then added to another 50-liter bioreactor containing the already sterilized phytosterol composition as shown below.

The phytosterol composition, obtained from rapeseed oil (100 gm), is mixed with silicone (1.6 liters) and heated to 100–130° C. to obtain a paste. This paste is then transferred to a 50-liter bioreactor containing 15 liters of salt medium of the same composition as in Example 1. The entire contents is sterilized at 120° C., and cooled to room temperature. The portion (1.5 liters) of innoculum, as noted above, is now transferred to this bioreactor and the fermentation allowed to proceed at 35° C. for a period of 48 h. GLC monitoring revealed that, by this time, a 90% bioconversion of the phytosterol composition had taken place. The initial pH of 7.2 had slightly altered to a value of 7.4.

The separate silicone layer, containing AD, was extracted with acetonitrile (3×0.7 liters), and the solvent evaporated to afford the crude product. Crystallization of the crude AD utilizing hydrocarbon solvents (n-pentane or n-hexane) containing n-butanol (2–5%) or isopropanol (2–5%), afforded an excellent recovery (>90%) of pure AD (purity >96%).

The remaining innoculum (3.5 liters) prepared as noted above is now used in Example 3.

EXAMPLE 3

The innoculum remaining (3.5 liters) from Example 2 is utilized in this larger scale experiment.

The phytosterol composition, obtained from rapeseed oil (900 gm, concentration at 30 gm/liter) is placed in a 50-liter bioreactor, dissolved in polypropylene glycol (8 liters) by heating to 100–130° C. and the contents cooled to room temperature. The innoculum (3.5 liters) is added and the fermentation allowed to proceed for a period of 18–25 days (see Experiment 10, Table 1). As in Example 1, this larger scale experiment similarly revealed a change from the initial pH of 7.0 to 5.5 at harvest time. GLC monitoring indicated a bioconversion of 80%. Extraction of the fermentation mixture with chloroform provided an extract containing polypropylene glycol and AD.

EXAMPLE 4

The innoculum of Mycobacterium MB 3683 is prepared it six 2-liter Erlenmeyer flasks each containing 500 ml of the following medium (gm/liter): glucose (10 gm), peptone (10 gm), yeast extract (3 gm) and malt extract (20 gm) and allowed to grow for 2 days during which time the pH remained at 7.0.

The innoculum (2 liters) from the Erlenmeyer flasks is then transferred to a 30 liter bioreactor containing 20 liter of the Refiners molasses-inorganic salt medium of Example 1 and grown for 16 hours. The latter innoculum (20 liters) was then transferred to a 400 liter bioreactor containing 200 liters of the inorganic salt medium of Example 1.

The phytosterol composition obtained from rapeseed (one kilogram, concentration of 5 gm per liter of nutrient medium) is dissolved in PPG (ten liters, concentration of 100 gm per liter) by heating at 115 C. to form a paste. This paste is then transferred to the 400 liter bioreactor and the fermentation allowed to proceed for a total of 115 hours under the following conditions: aeration of one liter per minute, stirring at 200 rpm, temperature of 35 C. The pH varied slightly from 6.45 to 6.6 at the time of harvest.

In order to assess the rate of bioconversion, aliquots of the fermentation mixture were withdrawn and analyzed. The following levels of bioconversion to AD were observed: 20 hours (10%), 44 hours (20%), 68 hours (50%), 91 hours (80%), 115 hours (90%). Extraction with chloroform, as in Example 1, affords an extract containing PPG and AD.

EXAMPLE 5

This experiment is a repeat of Example 4 except that the solubilizing agent is silicone in place of PPG.

The phytosterol composition (one kilogram) is dissolved in silicone (20 liters) by heating to 130 C. to form a paste. This paste is transferred to the 400 liter bioreactor containing 200 liters of the nutrient medium as in Example 4. Fermentation under the conditions summarized in Example 4 and for a period of 120 hours, completed the bioconversion to AD. Extraction, of the silicone layer, as in Example 2, with acetonitrile, followed by crystallization, afforded AD in 90% yield.

While particular aspects, embodiments and applications of the present invention have been shown and described, it will be understood, of course, that the invention is not limited thereto, since modifications may be made by those skilled in the applicable technologies, particularly in light of the foregoing description. The appended claims include within their ambit such modifications and variants of the exemplary embodiments of the invention described herein as would be apparent to those skilled in the applicable technologies.

TABLE 1

Summary of Results - Fermentation of Phytosterol Mixtures to AD

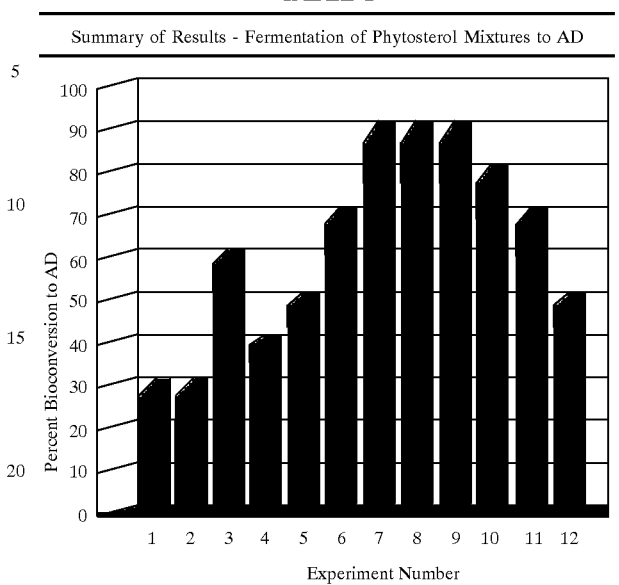

| Exp. No. | Conc. Phytosterols (gm) per L of medium | Conc. Phytosterols per Vol. of Solubilizing Agent | Time (Days) | Percent of Bioconversion |
|---|---|---|---|---|
| 1 | 5 | 1 Kg/L oil[a] | 7 | 30 |
| 2 | 5 | 1 Kg/L oil[a] | 7 | 30 |
| 3 | 5 | 1 Kg/L PPG[b] | 7 | 60 |
| 4 | 5 | Micronize - no agent | 10 | 40 |
| 5 | 5 | 1 Kg/L oil[a] | 7 | 50 |
| 6 | 5 | 1 Kg/L PPG[b] | 7 | 70 |
| 7 | 5 | 100 gm/L PPG[b] | 7 | 90 |
| 8 | 10 | 100 gm/L PPG[b] | 12 | 90 |
| 9 | 5 | 50 gm/L PPG[b] | 6 | 90 |
| 10 | 30 | 100 gm/L PPG[b] | 25 | 80 |
| 11 | 5 | 200 gm/L PPG[b]/L oil[a] | 12 | 70 |
| 12 | 5 | Steam - no other additives | 14 | 50 |

[a]sunflower oil
[b]polypropylene glycol

What is claimed is:

1. A process of fermenting a phytosterol composition to produce androstenedione (androst-4-ene-3, 17-dione) and androstadienedione (androsta-1, 4-diene-3, 17-dione) that comprises:
   propagating a Mycobacterium MB 3683 culture in a nutrient medium;
   dissolving a phytosterol composition using one or more solubilizing agents into a solution; and
   placing the culture and the solution in a bioreactor for a sufficient time to transform the solution to androstenedione and androstadienedione.

2. The process of claim 1 wherein the phytosterol composition is extracted from Tall Oil soap.

3. The process of claim 1 wherein the phytosterol composition is derived from a suitable selected vegetable oil.

4. The process of claim 3 wherein the vegetable oil is selected from the group comprising soy, rapeseed, corn, cottonseed, sunflower, olive, linseed, or rice bran.

5. The process of claim 1 wherein the solubilizing agent is a member of the glycol family.

6. The process of claim 1 wherein the solubilizing agent is polypropylene glycol.

7. The process of claim 1 wherein the solubilizing agent is a member of the silicone family.

8. The process of claim 1 wherein the solubilizing agent is silicone.

9. The process of claim 1 wherein the nutrient medium comprises Refiners molasses and inorganic salts.

10. The process of claim 1 wherein the fermentation is carried out aerobically.

* * * * *